United States Patent [19]
Obagi et al.

[11] Patent Number: 5,827,884
[45] Date of Patent: *Oct. 27, 1998

[54] SKIN PEEL MAINTENANCE COMPOSITION AND METHOD

[75] Inventors: Zein E. Obagi, Beverly Hills; George H. Michel, Glendora, both of Calif.

[73] Assignee: OMP Acquisition Corporation, Torrance, Calif.

[ * ] Notice: The term of this patent shall not extend beyond the expiration date of Pat. No. 5,166,176.

[21] Appl. No.: 672,797

[22] Filed: Jun. 28, 1996

Related U.S. Application Data

[63] Continuation-in-part of Ser. No. 528,782, Sep. 15, 1995, abandoned.

[51] Int. Cl.$^6$ .................................................. A61K 31/19
[52] U.S. Cl. ............................................. 514/557; 424/63
[58] Field of Search .................... 424/401, 63; 514/859, 514/770, 844, 557; 562/602

[56] References Cited

U.S. PATENT DOCUMENTS

| | | | |
|---|---|---|---|
| 3,620,919 | 11/1971 | Hardman | 435/267 |
| 3,821,370 | 6/1974 | Tenta | 424/642 |
| 3,949,072 | 4/1976 | Tenta | 424/642 |
| 3,949,741 | 4/1976 | Hofmann | 606/204.35 |
| 3,992,315 | 11/1976 | Dibb et al. | 536/5 |
| 4,112,121 | 9/1978 | Tenta | 514/731 |
| 4,187,291 | 2/1980 | Marissal | 424/94.62 |
| 4,874,361 | 10/1989 | Obagi | 604/20 |
| 4,938,969 | 7/1990 | Schinitsky et al. | 424/642 |
| 5,011,693 | 4/1991 | Whitefield | 424/455 |
| 5,022,413 | 6/1991 | Spina, Jr. et al. | 128/898 |
| 5,166,176 | 11/1992 | Obagi et al. | |
| 5,415,861 | 5/1995 | Duffy et al. | 424/401 |
| 5,505,948 | 4/1996 | Rapaport | 424/401 |
| 5,730,991 | 3/1998 | Rapaport | 424/401 |

FOREIGN PATENT DOCUMENTS

| | | |
|---|---|---|
| 55-031057 | 5/1980 | Japan . |
| 920238751 | 9/1992 | Japan . |
| 9503779 | 2/1995 | WIPO . |
| 9503811 | 2/1995 | WIPO . |

OTHER PUBLICATIONS

Beeson, W.H. et al., "Chemical Face Peeling Without Taping", J. Dermatol. Surg. Oncol., vol. 11, No. 10, Published in 1985, pp. 985–990.
Parish, L.C., "Chemexfoliation: Legitimate Medicine or Quakery?", Drug Therapy, vol. 19, No. 3, Published in 1989, p. 112.
Pesko, L.J., "Compounding: Chemexfoliation", American Druggist, vol. 210, No. 2, Published in Jun. 1994, pp. 45–46.
Matarasso, S.L., et al., "Wood's Lamp for Superficial Chemical Peels, Journal of the American Academy of Dermatology", Vol. 30, No. 6, Published in 1994, pp. 988–992.

*Primary Examiner*—Robert H. Harrison
*Attorney, Agent, or Firm*—Brown, Martin, Haller & McClain, LLP

[57] ABSTRACT

A dermatological treatment and composition therefor are described for periodic and effective maintenance of a skin peel patient's subsequent skin condition. The treatment does not use radiation, can be performed quickly, is readily controlled by visual observation of the applied composition, and is self-limiting. The method includes forming a composition having a visualizing agent, a surfactant and an acid or acid equivalent dispersed in a carrier liquid, the concentration of the last not exceeding 30%; applying the composition to a predetermined area of the patient's skin in a quantity effective to result in a predetermined degree of mild exfoliation of the skin; determining degree of coverage of the area of skin by visual observation of extent of the visualizing agent; and maintaining the composition in contact with the area of skin for a period of time effective to result in the predetermined degree of exfoliation of the skin. Composition of this type are also disclosed. Preferable the acid or acid equivalent will be trichloroacetic acid and the surfactant will be a saponin or complex of saponins, preferably steroid saponins. The concentrations of the three principal ingredients, the amount of the composition used and the length of time of the application and treatment will vary according to the specific depth of peel or degree of maintenance which the dermatologist believes appropriate for a particular patient.

41 Claims, No Drawings

SKIN PEEL MAINTENANCE COMPOSITION AND METHOD

CROSS REFERENCE TO RELATED APPLICATION

This application is a continuation-in-part of application Ser. No. 08/528,782, filed Sep. 15, 1995, abandoned, of like title.

BACKGROUND OF THE INVENTION

1. Field of the Invention

The invention herein relates to dermatology. More particularly it relates to a method and composition for light maintenance of previously treated skin.

2. Description of the Prior Art

Skin peels for treatment of damaged skin have been used by dermatologists for some time. Several different types of peeling treatments or protocols have been described in the literature. One of the more significant treatments is one which we have described in our previous patents, U.S. Pat. Nos. 4,874,361 and 5,166,176. This treatment uses a novel composition including tricholoroacetic acid (TCA), a surfactant, and an emulsifier which is spread over the affected skin area. The covered skin area is then subjected to ultraviolet radiation. The resulting peel yields a new layer of vibrant, evenly colored, healthy skin, usually with only a single application. Skin peel treatments are commonly applied to facial skin, since people's faces are subjected to wind, sun, cold, abrasion and other types of damage with more frequency than is the skin on other parts of their bodies. Skin peel treatments are not so limited, however, and may be used for treatment of any damaged skin surface. Typical examples of such initial or "deep" peel treatments are described in the aforesaid U.S. Pat. No. 4,874,361.

As with any skin peel, however, the effects are not entirely permanent. The patient will after the treatment of course again be subjected to ambient conditions of sun and wind exposure, skin drying, and other environmental conditions which vary from patient to patient, but which all have an adverse effect on the treated skin. Since these adverse effects build up slowly over time, they can be minimized and the patient's skin restored to its initial post-treatment condition by periodic "maintenance" treatments. Such maintenance treatments must, however, be mild, easily performed and not uncomfortable for the patient.

In the past it has not been possible for physicians to observe any easily visible feature of the patient's skin or the prior art treating compositions to allow the physician to readily control such maintenance treatments with any degree of certainty or consistency. Consequently dermatologists have had difficulty in prescribing and conducting equivalent maintenance programs for their patients. It would therefore be valuable to both physician and patient if there were a maintenance treatment method or protocol which could be readily followed and which would allow the dermatologist to be able to consistently obtain predetermined degrees of skin maintenance for all patients.

SUMMARY OF THE INVENTION

The invention herein is a dermatological treatment and an novel composition therefor which permit periodic and effective maintenance of a patient's skin condition. The invention is also useful for patients requiring a less stringent initial peel since their skin condition requires less correction, and for patients whose skin has previously been subjected to a "skin peel" treatment for repair of damaged skin. It is particularly effective for maintenance of skin condition of patients who have undergone the skin peel treatment described in U.S. Pat. Nos. 4,874,361 and 5,166,176, although it may also be effectively used for maintenance of the skin condition of patients who have undergone other types of skin peeling treatments. The treatment of this invention does not require the use of radiation (particularly ultraviolet light radiation), can be performed in a few minutes and is readily controlled by the dermatologist merely by visual observation of the application of the composition to the patient. It thus provides not only for maintenance, but also can be used as a complete peel treatment with the flexibility to produce varying degrees of peel depth treatment, especially light peels. It also has the advantage of being self-limiting, in that the quantity of composition applied determines the depth of peel to be obtained. Once the composition has fully reacted with the skin proteins, no further peel occurs and the residual composition can be washed off.

In one embodiment the invention comprises a method for treating a human patient's skin without subjecting the patient to light radiation which comprises forming a composition comprising a visualizing agent, a surfactant and an acid or acid equivalent dispersed in a carrier liquid, the concentration of the acid or acid equivalent not exceeding 30% in the composition; applying the composition to a predetermined area of the patient's skin in a quantity effective to cause a predetermined degree of exfoliation of the skin; determining degree of coverage of the area of skin by visual observation of extent of appearance of the visualizing agent; and maintaining the composition in contact with the area of skin for a period of time effective to cause the predetermined degree of exfoliation of the skin.

In another embodiment, the invention comprises a composition for treating a human patient's skin without subjecting the patient to light radiation which comprises a visualizing agent, a surfactant and an acid or acid equivalent dispersed in a carrier liquid, the concentration of the acid or acid equivalent not exceeding 30% in the composition.

Preferable the acid or acid equivalent will be trichloroacetic acid. Acid equivalents such as resorcinol or phenol may also be used, but are not preferred. Preferably the surfactant will be a saponin or mixture or complex of saponins, preferably a mixture or complex of steroid saponins. The visualizing agent may be one that imparts color, texture, or other visible property to the composition.

Preferably the acid concentration will be in the range of 2%–25%, more preferably 10%–22%.

The concentrations of the three principal ingredients in the composition and the length of time of the application and treatment will vary according to the specific degree and intensity which the dermatologist believes appropriate for a particular patient.

The method and composition are uniquely suited to simple treatments of patients in a clinical setting and may be performed on an as-needed basis for each individual patient. The frequency of treatment needed by a particular patient will depend on that patient's exposure to debilitating influences, such as the extent of time the patient spends outdoors or in other adverse environments, the severity of the patient's initial skin condition, the patient's natural skin coloration, the sensitivity of the patient's skin, and such other factors as the dermatologist may consider important with respect to the particular patient.

DETAILED DESCRIPTION AND PREFERRED EMBODIMENTS

The invention is best understood by considering the composition first and then the method of its use to provide the maintenance treatment.

The composition has three principal components: an acid or acid equivalent, a surfactant and a visualizing agent, all contained in an inert liquid carrier. The acid or acid equivalent (sometimes collectively referred herein as the "acid") is preferably tricholoroacetic acid ($CCl_3COOH$; sometimes abbreviated herein as "TCA"). While other known peeling agents such as resorcinol or phenol could be used, their efficacy and controllability in this method are not expected to be as consistent as that of TCA, and therefore they are not preferred. The acid or acid equivalent, preferably TCA, will be present in a concentration not to exceed 30%. (All percentages are by weight per unit volume unless otherwise noted.) The preferable range of concentration will be about 2%–25%, preferably 10%–22%. Since TCA is commercially available at 30% concentration, the physician may normally incorporate it into the mixture at that concentration or may dilute it to a desired concentration upon combination with the other ingredients. Particular preferred compositions contain 15%, 20% and 25% TCA, respectively.

The surfactant is present to reduce surface tension of the composition, ameliorate the tendency of the acid to cause skin irritation and inflammation and to provide cell growth stimulatory activity. The general properties of surfactants are well known, and in the present invention the surfactant component acts in part to cause the acid to be evenly and thoroughly distributed across the treated area of skin and to penetrated uniformly into the dermal layers. The surfactants which are of use in the present invention are those which also have, in addition to their surfactant properties, cell growth stimulatory activity. There are a number of such surfactants, of both plant and animal origin. Typical examples are epidermal growth factor and fibroblast growth factor. Preferred, however, are the saponins, particularly the steroid saponins, since they accommodate being diluted with TCA and the visualizing agent and yet remain stable and effective. The saponins are a well known class of glycoside which are widely distributed in plants. They are commonly divided into two subclasses, the triterpenoid saponins, which are based on a pentacyclic triterpene structure, and the steroid saponins, which are based on a steroid nucleus. The saponins are well described in McIlroy, *The Plant Glycosides*, chapter IX (1951) and Noller, *Chemistry of Organic Compounds*, chapter 42 (3rd edn., 1965). Among the steroidal saponins are sarsaogenin and numerous similar compounds, usually containing additional hydroxyl and/or keto groups and/or double bonds, such as diosgenin, tigogenin and yuccagenin. Since many of these are naturally occurring materials, they are not necessarily isolated into individual compounds for use in the present composition. Both the individual compounds as synthesized or extracted and the mixtures will be suitable for use in the present invention, since for the purposes of this invention the saponins, particularly the steroid saponins, essentially all possess the necessary surfactant/growth stimulation properties. It is also possible that in some applications the saponins may be used in the form of the plant sources without direct isolation of the saponin component. A particularly preferred saponin is a proprietary steroid saponin composition known as "Complex 272" which is commercially available from the Mikuda Company, Glendora, Calif., and which has been approved by the U.S. Food and Drug Administration under 21 C.F.R. § 121.1163. "Complex 272" is a non-toxic saponin product derived from plants by extraction and fractional separation, and can be described as an amorphous colloidal glycoside with a steroid nucleus. It exhibits surface activating characteristics, is soluble in water and is stable to the relevant temperatures. Other properties of the saponins are described in the aforementioned U.S. Pat. No. 5,166,176.

The surfactant, preferably a steroid saponin, will be present in the composition in a concentration of approximately 0.01% to 2.0%. The exact concentration will depend on the degree of treatment intended and on the particular surfactant used. If greater depth of effect is desired, more surfactant can be used. On the other hand, surfactants are known to have varying degrees of toxicity, which must be considered in determining selecting the surfactant and its concentration. Toxicity of saponins is discussed in McIlroy, supra, and Gennaro, *Remington's Pharmaceutical Sciences*, chapter 25 (17th edn., 1985). In the present compositions, however, the dermatologist will have no difficulty selecting the appropriate saponin composition and concentration for a particular treatment. A particularly preferred steroid saponin composition is one known as "Complex 272," commercially available from the Mikuda Company, which has been approved for use by the U.S. Food and Drug Administration under 21 C.F.R. § 121.1163. The steroid saponin helps create a homogeneous mixture between the TCA and the other materials, facilitates an even dispersion of TCA in the mixture and smooths the application of the mixture on the skin surface. It also helps regulate the release of TCA to the skin surface, thus allowing for faster neutralization of the TCA by skin protein.

The third ingredient of the compositions is a visualizing agent. This may be any compound or material which does not affect the efficacy of the acid or the surfactant, which is also nontoxic and substantially harmless to the patient's skin, and which imparts to the composition some type of property which renders the composition visible to the dermatologist when applied to the patient's skin. The visible property may be color, texture, light reflection or refraction, or anything else which the dermatologist can see. The purpose of the visualizing component is to permit the dermatologist to determine precisely the areal extent and thickness of the applied composition in order to monitor the progress of the treatment. The properties most readily obtained with commercially available materials are color, texture and film opacity. Color may be obtained from dyes, materials which are themselves naturally colored, or materials which in the presence of the acid or the surfactant acquire a color. Care must be taken when selecting dyes, however, since they should color only the composition itself and not impart any significant or permanent color (either the dye color or some other color) to the patient's skin. Such not only disfigures the patient, but also may make it difficult for the dermatologist to effectively monitor the progress of the treatment, since the color imparted to the patient's skin may obscure the actual extent of coverage of the composition on the skin. A typical colorant which can be used as the visualizing component is methylene blue [3,7-bis(dimethylamino)phenothiazin-5-ium chloride: $C_{16}H_{18}ClN_3S$], which imparts a blue color to the composition. Preferred are lake food colorants, particularly the tetramethylene colorants such as FD&C Blue No. 1; these are described in Considine (ed.), *Van Nostrand's Scientific Encyclopedia*, (7th edn.: 1989), vol. 1, pp. 702–703. Texture or film opacity are best obtained by addition of inert granular materials, such as granular silica or titanium dioxide, which can be seen by the dermatologist. The extent of the application of the composition is observed by comparison of the visual texture of the composition layer with the texture of the adjacent uncovered portion of the patient's skin. The visual effect can often be enhance by viewing the applied composition and adjacent skin at a slight angle or with a light angled to cause the composition's texture to produce shadows. The granule size range will be centered around a particle size which is sufficiently large to be readily visible but no so large as to act as an abrasive. The lower limit of visibility to the unaided eye is about 50 μm particle diameter, so the portion of the granulated materials smaller than that should be minimized or eliminated as by screening. It is also helpful if the granulated material also has some degree of coloration, so that the dermatologist can rely on both texture and color for observation of the visualizing component. Granulated colored quartz and $TiO_2$ can be effective in this regard. The visualizing component will be present in an amount only sufficiently large to produce a reasonable visual effect which can easily be observed by the dermatologist. Greater amounts will be unnecessary and may adversely affect the efficacy of the active acid or surfactant components. The exact concentrations used will vary widely depending on the nature of the visualizing agent (e.g., colorant versus texturizing material) and on the ability of the specific material chosen to produce the visual effect (e.g., a high intensity dye versus a compound producing a light tint). Generally the visualizing component will be present as less than 2% of the composition.

Other materials which may be present in small amounts, but which must not adversely affect the efficacy of the acid, surfactant or visualizing component, may include humectant-emollients, antioxidants, emulsifiers and preservatives. Such materials are described in the aforesaid U.S. Pat. No. 5,166,176. One such preferred material is cetyl alcohol (n-1-hexadecanol), which improves the viscosity of the mixture, helps stabilize the consistency and facilitates compatibility between TCA and the other materials by preventing TCA separation.

All ingredients will be dispersed or dissolved in a suitable inert liquid carrier, most commonly water, which may be deionized. The carrier comprises the balance of the overall treating composition. One preferred composition may conveniently be formed by combining acid at the commercial 30% concentration with an equal quantity of base (i.e., the carrier in which are dissolved or dispersed the surfactant and visualizing agent, as well as any supplemental ingredients), so that the acid is diluted to 15% working concentration. This composition is particularly useful for normal, sensitive, dry or thin skin. Another preferred composition may conveniently be formed by combining two volumes of acid at the commercial 30% concentration with one volume of base, so that the acid is diluted to 20% working concentration. This composition may be used when the patient has thick skin or can tolerate a more intense sensation during the procedure. Other ratios of acid and base may also be used, or more concentrated quantities may be combined and then diluted to the final desired concentrations of the ingredients by addition of carrier liquid.

The treatment of this invention comprises applying the composition to the affected skin area of the patient using a small gauze pad, allowing the composition to remain in place for at least a minimum of five minutes. The amount of time allotted for the peel is selected based on the physician's predetermination, for the particular patient, of the desired degree of exfoliation of the upper dermal layers. Since the compositions herein are self-limiting in their reaction, the time and depth of peel will be determined by the amount of the composition used. One or two subsequent coats may be applied after the first coat, with a 2–3 minute wait between coat applications. Each application will be accompanied by a burning sensation noticeable by the patient, but tolerable. The sensation may be more intense for the deeper skin layers. Usually up to three coats will be used to penetrate the basal skin layer, with the next (usually fourth) coat penetrating the papillary dermis and effecting a light peel rather than being an exfoliation procedure. Such a peel coat can be applied over the entire treatment area or just to specific areas where more depth is needed to correct wrinkles, large pores or light scars.

Once the reactants, particularly the acid, have fully reacted with the proteins in the skin, the composition and the exfoliation products then are removed, most conveniently by wiping with an alcohol. The actual relationship of the time, depth of peel and quantity of composition will differ among the different patients because of different skin conditions. Dermatologists are well aware of these differences in skin condition, and will have no difficulty determining the appropriate amount of composition to be used for a particular patient. In any case where there is doubt, a small amount of composition can be used in a very mild first peel and then the procedure can be repeated as needed after the effects of that first peel are observed.

The invention herein is a result of our discovery that, unlike in regular skin peel treatments involving use of ultraviolet radiation, which can be focused and precisely timed, it is very difficult for the dermatologist to regulate the uniformity and extent of coating with prior art maintenance compositions, in order to obtain the precise degree of maintenance peel which is desired. With the radiative treatments, there is a distinct appearance change of the coated composition as the radiation produces exfoliation of the skin proteins, with an appearance which may be described as "frost-like" gradually becoming visible as the deep peel treatment progresses. This is not substantial enough in a light or maintenance peel to be usable as an indicator. Neither have the prior art methods or compositions provided any alternative readily visible guide for the physician to be able to observe easily the extent of the maintenance peel treatment. The present invention overcomes those deficiencies by incorporating a unique visualizing agent, which makes the extent of coverage of the maintenance peeling composition on the patient's skin immediately and unequivocally apparent. It also permits visualization of the uniformity and thickness of the coating layer, by means of the relative degree of transparency of the layer and by being able to clearly observe these properties of the peel composition layer on the patient's skin. The objective is to create an even visual appearance (e.g., an even blue coloration) over the treatment area without skipping any portions. Thus the visualizing agent in the composition allows the amount of composition itself to be applied evenly and over a known and observable area of the patient's skin. The visualizing agent (e.g., a blue lake colorant) is readily removed by alcohol or cleanser after the reaction. The TCA reaction binds the skin protein and does not require neutralization.

Normally the actual maintenance peeling of the skin will not occur during the treatment itself. Rather the ability of the physician to closely control the degree of treatment with the maintenance composition of this invention insures that when the treated skin actually exfoliates over the hours or days following the treatment, the resulting degree of exfoliation will be precisely what the dermatologist had intended. During this period the patient will normally be allowed to wash his or her skin with mild soap or topical cleanser formulations, a number of which are available commercially. An antibiotic soap or topical antibiotic cream may be advised in some cases, if there is a risk of dermal infection. The physician may also advise the use of a suitable benzoyl peroxide cream or retinoic acid during the exfoliation period, to enhance cell regeneration in the affected area.

Subsequently as the exfoliation becomes completed, mild moisturizing creams may be applied to reduce any chapping or other irritation which may occur.

The process and composition of the present invention have been tested and found to be effective and easily accomplished. In one example, a composition was formulated by making a 30% solution of TCA in a quantity of sterile water. An equal quantity of sterile water was used to dissolve or suspend 0.15% of the Complex 272 saponin mixture or complex and 0.10% of methylene blue. These two quantities were combined to form the final composition which had a TCA concentration of 15%. This was applied to the skin of a patient who had some months previously had a regular skin peel for the affected area. The composition was manually applied as a coating and its uniformity of depth and areal extent were readily observed by the clearly visible blue color and uniform degree of transparency. After five minutes the treated area was washed with a gauze pad containing alcohol. The alcohol wash removed the minor amount of blue coloration which had transferred to the patient's skin. Over the period of the next four days the patient's skin underwent a mild exfoliation, with the degree of exfoliation being substantially uniform over the affected area and of the degree which the physician anticipated obtaining.

In another preferred composition, the base mixture contains 2.0% cetyl alcohol, 0.2% F.D.&C. Blue No. 1 and 0.15% Complex 272 saponin, as well as various stabilizers and lubricants, all dissolved or suspended in deionized water. One or two volumes of 30% TCA are added to one volume of this base to form a 15% or 20% TCA treatment composition, respectively.

The treatment method and compositions of this invention may be used for any affected skin area. As noted above, skin peeling is commonly used for repair of damaged facial skin, since facial skin is usually exposed to more severe environmental and ambient conditions than other skin areas of a person's body, so the present invention will find extensive use for facial skin maintenance. Further, since treated facial skin is also subjected to more aggressive environmental and ambient conditions after the initial treatment, maintenance is normally needed at more frequent intervals than for other skin areas. Most patients are also quite conscious of their appearance, and are more likely to seek more frequent maintenance treatments to preserve the desirable appearance of their treated facial skin. However, also as noted, the maintenance treatments of the present invention are not limited only to facial skin, but can advantageously be used for maintenance of treated skin on all parts of the body.

It will be evident that there are numerous embodiments of this invention which, while not expressly described above, are clearly within the scope and spirit of the invention. The above description is therefore intended to be exemplary only, and the actual scope of the invention is to be determined solely from the appended claims.

We claim:

1. A method for treating a human patient's skin to cause exfoliation without subjecting the patient to skin peeling ultraviolet light which comprises:

forming a composition comprising a visualizing agent, a surfactant and an acid or acid equivalent dispersed in a carrier liquid, the concentration of the acid or acid equivalent not exceeding 25% in said composition;

applying said composition to a predetermined area of said patient's skin in a quantity effective to cause a predetermined degree of said exfoliation of said skin;

determining degree of coverage of said area of skin by visual observation of extent of appearance of said visualizing agent; and maintaining said composition in contact with said area of skin for a period of time effective to result in said predetermined degree of exfoliation of said skin.

2. A method as in claim 1 wherein said concentration of acid or acid equivalent does not exceed 25%.

3. A method as in claim 2 wherein said concentration of acid or acid equivalent is in the range of 2%–25%.

4. A method as in claim 3 wherein said concentration of acid or acid equivalent is in the range of 10%–22%.

5. A method as in claim 1 wherein said acid or acid equivalent comprises trichloroacetic acid.

6. A method as in claim 1 wherein said surfactant comprises a saponin.

7. A method as in claim 6 wherein said saponin comprises a steroid saponin.

8. A method as in claim 6 wherein said surfactant comprises a complex of saponins.

9. A method as in claim 8 wherein at least one saponin in said complex of saponins is a steroid saponin.

10. A method as in claim 1 wherein said visualizing agent is selected from the group consisting of materials whose visibility is due to color, texture, light reflective or light refractive properties or ability to produce film opacity.

11. A method as in claim 10 wherein said visualizing agent is selected from the group consisting of materials whose visibility is due to their color, texture or ability to produce film opacity.

12. A method as in claim 11 wherein said visualizing agent is selected from the group consisting of materials whose visibility is due to their texture or ability to produce film opacity.

13. A method as in claim 12 wherein said visualizing agent is particulated silica or titanium dioxide.

14. A method as in claim 11 wherein said visualizing agent is selected from the group consisting of materials whose visibility is due to their color.

15. A method as in claim 14 wherein said visualizing agent is a colorant.

16. A method as in claim 15 wherein said visualizing agent is methylene blue or FD&C Blue No. 1 lake food colorant.

17. A method as in claim 1 wherein said carrier comprises water.

18. A method as in claim 17 where cetyl alcohol is present in said water.

19. A method as in claim 1 wherein said period of time is a minimum of five minutes.

20. A method as in claim 1 wherein said composition is formed by combination of a first liquid said acid or acid equivalent in a quantity of said carrier liquid at a concentration greater than its concentration in said composition and an equal quantity of a second liquid comprising said surfactant and said visualizing agent dispersed in said carrier liquid.

21. A method as in claim 20 wherein said acid or acid equivalent comprises trichloroacetic acid and said surfactant comprises a steroid saponin.

22. A composition for treating a human patient's skin to cause exfoliation without subjecting the patient to skin peeling ultraviolet light which comprises a visualizing agent, a surfactant and an acid or acid equivalent dispersed in a carrier liquid, the concentration of the acid or acid equivalent not exceeding 25%.

23. A composition as in claim 22 wherein said concentration of acid or acid equivalent does not exceed 25%.

24. A composition as in claim 23 wherein said concentration of acid or acid equivalent is in the range of 2%–25%.

25. A composition as in claim 24 wherein said concentration of acid or acid equivalent is in the range of 10%–22%.

26. A composition as in claim 22 wherein said acid or acid equivalent comprises trichloroacetic acid.

27. A composition as in claim 22 wherein said surfactant comprises a saponin.

28. A composition as in claim 27 wherein said saponin comprises a steroid saponin.

29. A composition as in claim 27 wherein said surfactant comprises a complex of saponins.

30. A composition as in claim 29 wherein at least one saponin in said complex of saponins is a steroid saponin.

31. A composition as in claim 22 wherein said visualizing agent is selected from the group consisting of materials whose visibility is due to color, texture, light reflective or light refractive properties or ability to produce film opacity.

32. A composition as in claim 31 wherein said visualizing agent is selected from the group consisting of materials whose visibility is due to their color, texture or ability to produce film opacity.

33. A composition as in claim 32 wherein said visualizing agent is selected from the group consisting of materials whose visibility is due to their texture or ability to produce film opacity.

34. A composition as in claim 33 wherein said visualizing agent is particulated silica or titanium dioxide.

35. A composition as in claim 32 wherein said visualizing agent is selected from the group consisting of materials whose visibility is due to their color.

36. A composition as in claim 35 wherein said visualizing agent is a colorant.

37. A composition as in claim 36 wherein said visualizing agent is methylene blue or FD&C Blue No. 1 lake food colorant.

38. A composition as in claim 22 wherein said carrier comprises water.

39. A composition as in claim 38 where cetyl alcohol is present in said water.

40. A composition as in claim 22 wherein said composition is formed by combination of a first liquid said acid or acid equivalent in a quantity of said carrier liquid at a concentration greater than its concentration in said composition and an equal quantity of a second liquid comprising said surfactant and said visualizing agent dispersed in said carrier liquid.

41. A composition as in claim 40 wherein said acid or acid equivalent comprises trichloroacetic acid and said surfactant comprises a steroid saponin.

* * * * *